United States Patent [19]

Aoyagi et al.

[11] Patent Number: 5,763,221

[45] Date of Patent: Jun. 9, 1998

[54] TRANSFORMANT PRODUCING SUBSTANCE PF1022, AND METHOD FOR TRANSFORMING MICROORGANISM BELONGING TO THE CLASS HYPHOMYCETES

[75] Inventors: Kaoru Aoyagi; Manabu Watanabe, both of Kanagawa; Kohji Yanai, Saitama; Takeshi Murakami, Kanagawa, all of Japan

[73] Assignee: Meiji Seika Kaisha, Ltd., Tokyo, Japan

[21] Appl. No.: 776,816

[22] PCT Filed: Jun. 19, 1996

[86] PCT No.: PCT/JP96/01692

§ 371 Date: Feb. 7, 1997

§ 102(e) Date: Feb. 7, 1997

[87] PCT Pub. No.: WO97/00944

PCT Pub. Date: Jan. 9, 1997

[30] Foreign Application Priority Data

Jun. 22, 1995 [JP] Japan ..................... 7-155973

[51] Int. Cl.$^6$ ................ C12P 21/02; C12N 9/30; C12N 15/09; C07K 5/12

[52] U.S. Cl. .................. 435/69.1; 435/254.11; 435/172.1; 435/203; 530/317

[58] Field of Search ................ 435/69.1, 254.11, 435/172.1, 203; 530/317

[56] References Cited

U.S. PATENT DOCUMENTS 5,116,815   5/1992   Takagi et al. .................. 514/11

OTHER PUBLICATIONS

Proc. Natl. Acad. Sci., USA, vol. 81, pp. 1470–1474, Mar. 1984: Transformation of *Aspergillus nidulans* by using a trpC plasmid by Yelton, Hamer and Timberlake.

Agric. Biol. Chem, 51 (2), pp. 323–328, 1987: Transformation of *Aspergillus oryzea* through Plasmid–mediated Complementation of the Methionine–auxotrophic Mutation by Iimura, Gomi, Uzu and Hara.

Curr Genet (1987) 11, pp. 499–503: Transformation of *Aspergillus niger* using the homologous orotidine–5'–phosphate–decarboxylase gene by Goosen, Bloemheuvel, Gysler, deBie, van den Broek & Swart.

*Primary Examiner*—Charles L. Patterson, Jr.
*Assistant Examiner*—Kawai Lau
*Attorney, Agent, or Firm*—Flynn, Thiel, Boutell & Tanis, P.C.

[57] ABSTRACT

A method for transforming strain PF1022, which produces a cyclic depsipeptide (substance PF1022) and belongs to the order Agonomycetales of the class Hyphomycetes has been established by using a plasmid constructed with a promoter, a terminator, a marker gene and a target gene. When the strain PF1022 was transformed by this method, a gene encoding an enzyme, which is the target gene, was transduced into the host. As a result, the utilization of nutrients by the strain PF1022 was improved and, further, its cyclic depsipeptide productivity was also improved.

6 Claims, 2 Drawing Sheets

TRANSFORMANT PRODUCING SUBSTANCE PF1022, AND METHOD FOR TRANSFORMING MICROORGANISM BELONGING TO THE CLASS HYPHOMYCETES

BACKGROUND OF THE INVENTION

1. Field of the Invention

The present invention relates to a transformant producing substance PF1022, which is a cyclic depsipeptide, a process for producing the substance PF1022, a method for elevating the productivity of the substance PF1022, and a method for transforming a microorganism belonging to the class Hyphomycetes.

2. Description of the Related Art

Microorganisms belonging to the class Hyphomycetes produce as metabolites various useful substances such as antibiotics, physiologically active substances and enzymes. Accordingly, for a long time, there have been studied and developed methods for obtaining such products by culturing these microorganisms on a large scale. As an example of common techniques for efficiently obtaining substances produced by microorganisms, a method which comprises artificially constructing mutants by, for example, UV irradiation or the use of a mutagenic agent and selecting a strain capable of producing the target substance in a large amount from among the mutants thus obtained is cited.

A strain newly constructed by such a method (hereinafter sometimes referred to as a highly productive strain) cannot always produce the desired metabolite at a high productivity in the same medium and under the same culture conditions as those for the parent strain thereof. Even though a highly productive strain is obtained by the above-mentioned technique, therefore, it is necessary to study, for every strain, medium and culture conditions suitable for the strain. In the case where a large fermentation tank is employed, in particular, the yield of the fermentation product widely varies depending on the medium and culture conditions, even when a highly productive strain which has been bred by the above-mentioned method is used. To efficiently obtain the desired metabolite, it is therefore necessary to study in detail the medium composition, the conditions for sterilizing the medium, the aeration-agitation rate, the pHs and temperatures of the medium and during the culturing of the highly productive strain, to determine and analyze various parameters relating to the culture, and to regulate the fermentation and metabolism based on the results.

Materials of the medium for culturing the microorganism are sometimes restricted so as to stabilize the fermentation conditions, etc., or acquire the desired substance economically. In order to achieve the efficient utilization of the medium materials as nutrients by the microorganism, however, it is necessary in some cases to impart novel genetic characters, which are necessary for altering the medium materials to substances the microorganism can utilize as nutrients, to the microorganism. In such a case, the impartment of these novel genetic characters by the usual mutagenesis treatment as described above is difficult. For these reasons, molecular breeding, which comprises transducing a specific alien gene into a specific microorganism by using genetic engineering techniques to thereby impart novel genetic characters to the microorganism, has been utilized. However, with respect to the microorganisms belonging to the class Hyphomycetes, which are different from bacteria, yeasts, etc., the transformation is frequently difficult, because, for example, there are known few autonomously replicating plasmids appropriate for the transformation of these microorganisms, many of which are polykaryocytes, and the frequencies of the protoplast generation and regeneration are extremely low. In fact, the transformation of microorganisms belonging to the class Hyphomycetes by genetic engineering techniques is practiced only by using fungi, for example, *A. nidulans* (see Proc. Natl. Acad. Sci., USA, 81, 1470(1984)), *A. oryzae* (see Agrc. Biol. Chem., 51, 323(1987)) or *A. niger* (see Curr. Genetics, 11, 499(1987)).

By the way, it has been known that some microorganisms belonging to the order Agonomycetales of the class Hyphomycetes produce useful substances, such as a cyclic depsipeptide having a vermifugal activity (i.e., substance PF1022) as described in, for example, Japanese Patent Publication-A No. 3-35796 (published on Feb. 15, 1991). If a method for transforming a microorganism belonging to the class Hyphomycetes is established, therefore, novel genetic characters advantageous for the production of substance PF1022 can be imparted by genetic engineering techniques to the above-mentioned microorganism producing substance PF1022. More particularly, by transducing into the microorganism producing substance PF1022 a gene which encodes a substance relating to the biosynthesis of substance PF1022 and thus can elevate substance PF1022 productivity, or a gene which encodes an enzyme, such as amylase, lipase, protease and cellulase, enabling the alteration of the medium materials, it is possible to have the novel genetic characters encoded by the gene expressed. Then, the obtained transformant is cultured and substance PF1022, or a substance (for example, a protein or a peptide) encoded by the alien gene transduced can be produced in a large amount. However, no method has been developed hitherto for the transformation of a microorganism producing the substance PF1022, since, for example, there has not been known the extent of the drug resistance and the promoter for the operation of the marker gene and the alien gene for the selection of a transformant, in addition to the difficulties in transformation which the above-mentioned microorganisms belonging to the class Hyphomycetes commonly have.

DISCLOSURE OF THE INVENTION

SUMMARY OF THE INVENTION

The present inventors have conducted extensive studies on a method for transforming strain PF1022, which is one of the microorganisms which produces the substance PF1022 (hereinafter referred to simply as substance PF1022-producing microorganisms in some cases) and belongs to the order Agonomycetales of the class Hyphomycetes. As a result of the studies, they have found that the above-mentioned microorganism can be transformed by a plasmid constructed with a promoter, a terminator, a marker gene and a target gene. The present inventors have further succeeded in the transformation of the strain PF1022 by using a plasmid prepared by ligating a target gene to a resistance gene expression cassette constructed with the promoter and terminator of a trpC gene carried by a microorganism originating in *Aspergillus nidulans* and a hygromycin B resistant gene, as the marker gene, carried by a microorganism originating in *Escherichia coli*. When the transformant obtained by the method has been cultured, the expression of a protein (enzyme) originating in the target gene transduced thereinto in a large amount has been confirmed, and, at the same time, the elevation of the productivity of the substance PF1022 has also been confirmed. The present invention has been completed based on these findings.

Thus, the present invention relates to a transformant producing substance PF1022 which is obtained by transforming a host producing the substance PF1022 by using a plasmid constructed with a promoter, a terminator, a marker gene and a target gene.

The present invention further relates to a process for producing substance PF1022 which comprises the step of culturing the above-mentioned transformant and the step of recovering the product from the culture thus obtained.

The present invention furthermore relates to a method for elevating the substance PF1022 productivity of a substance PF1022-producing microorganism which comprises transforming a host producing the substance PF1022 by using a plasmid constructed with a promoter, a terminator, a marker gene and, a gene encoding a substance relating to the biosynthesis of substance PF1022 and/or a gene encoding a substance relating to the utilization of nutrients by the host.

In addition, the present invention relates to a method for transformation which comprises transforming the strain PF1022 belonging to the order Agonomycetales of the class Hyphomycetes by using a plasmid constructed with a promoter, a terminator, a marker gene and a target gene.

Now, the present invention will be described in detail.

DETAILED DESCRIPTION OF THE INVENTION

The transformant of the present invention is one obtained by transforming a host producing substance PF1022 by using a specific plasmid. The substance PF1022 herein is a cyclic depsipeptide and, although its properties are described in detail in Japanese Patent Publication-A No. 3-35796 (published on Feb. 15, 1991), they are summarized as follows.

(1) Color and form: colorless crystals, (2) Melting point: 104° to 106° C.

(3) Molecular formula: $C_{52}H_{76}N_4O_{12}$ (4) Mass spectrum (EI-MS): m/z 948 (M$^+$), (5) Specific rotation: $[\alpha]_D^{22}$ −102° (c 0.1methanol)

(6) Solubility: soluble in methanol, ethyl acetate, acetone, chloroform and dimethyl sulfoxide but insoluble in water, (7) Distinction between basicity, acidity and neutrality: neutral substance, and (8) Chemical structural formula: as shown in the following formula (I):

microorganism which produces the substance PF1022 (hereinafter sometimes referred to as a substance PF1022-producing microorganism) As an example of the substance PF1022-producing microorganisms, the strain PF1022 belonging to the order Agonomycetales of the class Hyphomycetes [which has been deposited with National Institute of Bioscience and Human-echnology, Agency of Industrial Science and Technology (Higashi 1-1-3, Tsukuba-shi, Ibaraki, 305 Japan) since Jan. 24, 1989, and has now the accession number of FERM BP-2671]is cited. The strain PF1022 is a microorganism producing the above-mentioned substance PF1022 having a vermifugal activity and, although its properties are described in detail in Japanese Patent Publication-A No. 3-35796 (published on Feb. 15, 1991), its mycological properties are summarized as follows:

(1) Growth: It grows well on potato dextrose agar medium, potato carrot agar medium, malt extract agar medium and oatmeal agar medium at 25° C., but poorly on Czapek-Dox agar medium, Miura agar medium and corn meal agar medium at 25° C., and does not grow at 37° C.

(2) Morphology: It forms white and fluffy hyphae. The back of a colony is initially in a white or pale yellow color and then dark brown spots are formed thereon. No characteristic morphology such as a conidium is observed.

The strain PF1022 is liable to change in properties, which is observed in other molds. Needless to say, a mutant, a character conjugate or a gene recombinant originating in this strain is also usable as a host, so long as it produces the substance PF1022.

The plasmid for transformation to be used in the present invention is constructed with a cloning vector replicable in *E. coli* (for example, pUC vector, pTV vector, pBluescript or pBR 322) as the substrate and, in addition, a promoter functional in the host, a marker gene starting with the N-terminus, a target gene and a terminator functional in the host.

Although the promoter and terminator to be used in the present invention are appropriately selected depending on the host, they are not particularly restricted so long as they are those capable of exerting their functions in the host. When, for example, strain PF1022 is employed as the host, as a promoter and a terminator as the constituents of the plasmid, those originating in a microorganism belonging to the class Hyphomycetes are employed. Examples thereof include the promoter regions and terminator regions of

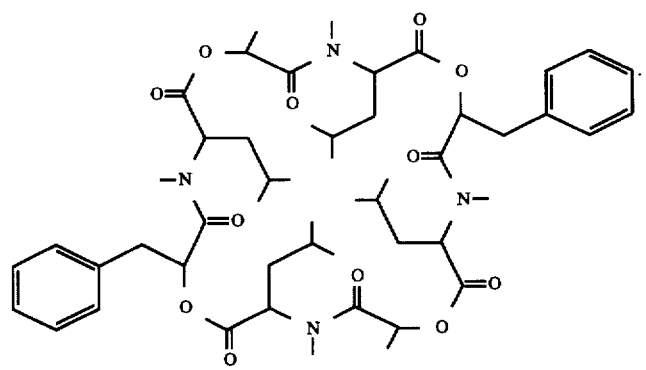

(I)

The host to be used for preparing the transformant of the present invention may be an arbitrary one, so long as it is a genes of enzymes participating in glycolysis such as 3-phosphoglycerate kinase, glyceraldehyde-3-phosphate dehydrogenase and enolase, genes of enzymes participating in the synthesis of amino acids such as ornithine carbamoyl transferase and tryptophan synthase, genes of hydrolases such as amylase, protease, lipase, cellulase and acetamidase, and genes of oxidoreductases such as nitrate reductase, orotidin-5'-phosphate dehydrogenase and alcohol dehydrogenase which originate in microorganisms belonging to the class Hyphomycetes.

The marker gene to be used in the present invention is not particularly restricted, so long as it is a gene encoding a certain character and usable as a marker for selecting transformed strains. Examples thereof include drug-resistance genes and those relating to auxotrophy. More particularly, a gene resistant to a certain drug to which the microorganism employed as the host has a sensitivity and a gene which, when the host is a certain auxotroph, imparts thereto a character by which the microorganism does not require the nutriment are used as the marker gene.

Examples of the drug-resistance gene include a hygromycin B-resistance gene carried by a microorganism originating in *E. coli*, a destomycin-resistance gene carried by a microorganism originating in *Streptomyces rimofaciens*, and a phleomycin-resistance gene carried by a microorganism originating in *Streptococcus hindustanus*. While, examples of the genes relating to auxotrophy include ArgB (see John, M. A. and Peberdy, J. F., Enzyme Microbiol. Technol. 6, 386–389(1984)) and trpC (see Yelton, M. M., Hamer, J. E. and Timberlake, W. E., Proc. Natl. Acad. Sci. USA, 81, 1470–1474(1984)) relating respectively to arginine and tryptophan requirements.

There have been known drug-resistance gene expression cassettes, for example, hyg'XbaI (see D. Cullen et al., Gene, 57, 21–26(1987)) which enables the expression of the hygromycin B-resistance gene carried by a microorganism originating in *E. coli* in a microorganism belonging to the class Hyphomycetes with the use of the promoter region and the terminator region of a trpC gene carried by a microorganism originating in *A. nidulans*, and such a cassette may also be used in the preparation of the plasmid according to the present invention. When the drug-resistance gene expression cassette thus constructed is ligated to another plasmid (for example, one having the gene encoding a desired enzyme) at a definite site and the host is transformed by the use of the thus-prepared plasmid, the drug resistance, which is the character originating in the drug-resistance gene contained in the above-mentioned cassette, can be utilized in order to screen the strain with the expression of the desired character (for example, an enzyme).

Although the target gene to be used in the present invention is not particularly restricted, examples thereof include genes expressing substances which relate to the utilization of nutrients in the culture of a transformant, in other words, enable the alteration of medium materials, more particularly, genes encoding enzyme proteins such as amylase, lipase, protease and cellulase; genes encoding substances which can contribute to the increase in the productivity of a useful substance biologically synthesized by the host, i.e., substance PF1022 in the present invention, and which relate to the biosynthesis of the useful substance; and genes encoding useful proteins homogenous or heterogeneous to the useful substance biologically synthesized by the host such as pectinase, chitinase and peptides. These genes may be either those originating in organisms or chemically synthesized ones.

As the plasmid constructed with a promoter, a terminator, a marker gene and a target gene according to the present invention, use can be made of, for example, pAMY-Hyg constructed by ligating an α-amylase gene originating in *A. niger* as the target gene to hyg'XbaI which is the above-mentioned drug-resistance gene expression cassette. *Escherichia coli* JM109/pAMY-Hyg, which is such a plasmid, has been deposited with the National Institute of Bioscience and Human-Technology, Agency of Industrial Science and Technology (Higashi 1-1-3, Tsukuba-shi, Ibaraki, 305 JAPAN) since Jun. 14, 1996, and has had an accession number of FERM BP-5569.

It is preferable in the present invention to apply, in the transformation of the host, a process comprising the steps of protoplast generation of the microorganism, polyethylene glycol treatment and culturing in a regeneration medium. More particularly, the cells of the microorganism are treated with a protoplast-generating enzyme solution in an isotonic sucrose solution, thus preparing protoplasts. The protoplasts are brought into contact with the plasmid according to the present invention and polyethylene glycol, thus incorporating the plasmid into the protoplasts. The obtained protoplasts are cultured in the regeneration medium in the presence of the drug for screening or in the absence of a specified nutrient required by the host. Thus, a transformant exhibiting the character expressed by the marker gene, for example, drug resistance or nonauxotrophy, can be obtained.

A transformant prepared by transforming a specific host by the use of a plasmid constructed with a promoter, a terminator, a marker gene and a target gene, produces a substance produced by the host and a substance, for example, a protein or a peptide, encoded by the target gene thus transduced thereinto by genetic engineering techniques. By culturing the transformant under appropriate conditions, therefore, it is possible to obtain the substance produced by the host in a high efficiency or to obtain the substance encoded by the target gene transduced thereinto.

More particularly, the transformant of the present invention can be cultured in a liquid medium comprising common components, for example, carbon sources, nitrogen sources, inorganic salts and growth factor components, by a known culturing method such as culturing methods under aerobic conditions, shaking culturing method, aeration-agitation culturing method and submerged culturing method. The pH of the medium is, for example, from about 7 to 8. The culturing conditions may be common ones employed in the culturing of the host. When the host is, for example, the strain PF1022 belonging to the class Hyphomycetes, the culturing of the transformant can be conducted in which the temperature is from 15° to 45° C., preferably from 15° to 30° C., and the culturing time is about 24 to 240 hours.

In the recovery from the culture of the substance produced by the transformant of the present invention which is obtained by culturing the transformant, more particularly, the substance PF1022 or another protein or peptide, use can be made of one or a suitable combination of the usual isolation procedures selected by taking the properties of the product into consideration, for example, solvent extraction, a method using an ion exchange resin, adsorption column chromatography, partition column chromatography, gel filtration, dialysis and precipitation.

According to the transformation method of the present invention, it is possible to transduce a gene encoding a substance affecting the utilization of nutrients of the microorganism (in other words, selection of the medium materials) such as amylase, lipase, protease and cellulase, or a gene encoding a substance relating to the biosynthesis of the substance PF1022 by the microorganism into the host (a PF1022-producing microorganism). As a result, the mass-production of the substance encoded by the transduced gene, and the economical and efficient production of the substance PF1022 become possible.

EXAMPLES

Figure 1:
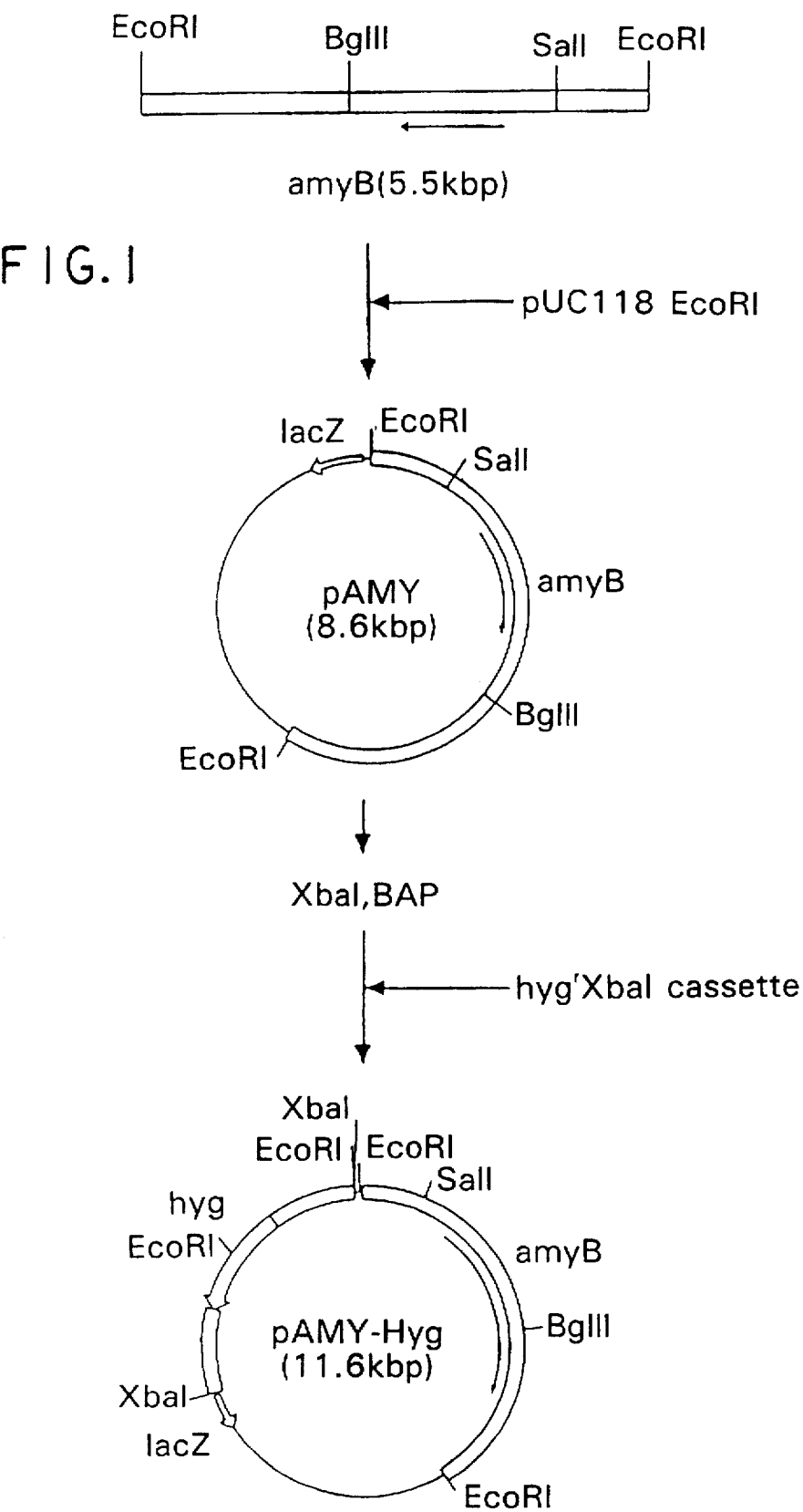
FIG. 1 is a flow sheet showing the process of the construction of pAMY-Hyg.

The present invention will now be illustrated in detail by referring to Examples, by which the invention should not be considered to be limited.

Example 1

Transformation of strain PF1022 by plasmid pDH25 (see D. Cullen et al., Gene, 57, 21–26 (1987))

As the seed medium for the strain PF1022, one comprising 2.0% of soluble starch, 1.0% of glucose, 0.5% of polypeptone, 0.6% of wheat germ, 0.3% of yeast extract, 0.2% of soybean cake and 0.2% of calcium carbonate and having a pH of 7.0 before sterilization was used.

The strain PF1022 was cultured in the above-mentioned seed medium at 26° C. for 48 hours. Then, those having hyphae were collected by centrifuging at 3,000 rpm for 10 minutes and washed with a 0.5M solution of sucrose. Those having hyphae thus obtained were subjected to protoplast generation by shaking in a 0.5M solution of sucrose containing 3 mg/ml of β-glucuronidase (mfd. by Sigma), 1 mg/ml of chitinase (mfd. by Sigma) and 1 mg/ml of zymolyase (mfd. by Seikagaku Kogyo) at 30° C. for 2 hours. The mixture thus obtained was filtered and the cellular residue was thus eliminated. The protoplasts were washed by centrifuging (2,500 rpm, 10 minutes, 4° C.) in SUTC buffer (0.5M sucrose, 10 mM Tirs-HCl (pH 7.5), 10 mM calcium chloride) twice, and then a $10^7$ /ml protoplast suspension was prepared with the SUTC buffer.

To the protoplast suspension was added a solution (TE, 10 mM Tris-HCl (pH 8.0), 1 mM EDTA) of the plasmid pDH25 having a concentration of 1 mg/ml at a ratio of 10 µl per 100 µl of the suspension, and the resulting mixture was allowed to stand under ice-cooling for 5 minutes. Then, 400 µl of a polyethylene glycol (PEG 6000) solution was added to the mixture and the obtained mixture was allowed to stand under ice-cooling for an additional 20 minutes.

After washing PEG 6000 with the SUTC buffer, the protoplasts treated as described above were suspended again in the SUTC buffer. The obtained suspension was layered together with a potato dextrose soft agar medium onto a potato dextrose agar medium (hereinafter referred to simply as PDA medium) containing 100 µg/ml of hygromycin B. Culturing was effected at 26° C. for 5 days to thereby allow the formation of colonies. Thus, the transformant colonies were obtained.

Example 2

Confirmation of hygromycin B resistance of transformants by plasmid pDH25

In Example 1, 300 strains of transformants were obtained. The transformation efficiency was 30 transformants per µg of plasmid pDH25. The parent strain (the strain PF1022) and 10 strains among these transformants were cultured in the above-mentioned PDA medium to confirm the resistance to hygromycin B thereof. As a result, the parent strain could not grow in the medium containing 100 µg/ml of hygromycin B, while all of the transformants tested showed resistance against hygromycin B at a concentration of 250 µg/ml.

Example 3

Construction of plasmid pAMY-Hyg

An EcoRI fragment (hereinafter referred to as amyB) of 5.5 kbp containing an α-amylase gene of A. niger was isolated by a known method with the use of a Taka amylase gene carried by a microorganism originating in A. oryzae obtained by a known method (see S. Wisel et al., Mol. Microbiol., 3, 3–14(1989), M. J. Gines et al., Gene, 79, 107–117(1989), S. Tada et al., Agric. Biol. Chem., 53, 593–599(1989), and Tsukagoshi et al., Gene, 84, 319–327 (1989)) as a probe. This fragment was ligated to the EcoRI site of pUC118 by a known method to thereby prepare the plasmid pAMY.

On the other hand, the plasmid pDH25 was partially digested with EcoRI and an XbaI linker was ligated to the fragment thus obtained. Then, the obtained gene was further digested with XbaI. Thus, a hygromycin-resistance gene expression cassette (hereinafter referred to as the hyg'XbaI cassette) which was constructed with the promoter and terminator regions of the trpc gene carried by a microorganism originating in A. nidulans and the hygromycin B-resistance gene carried by a microorganism originating in E. coli, was prepared as the XbaI fragment of 3 kbp. This fragment was inserted into the XbaI site of the plasmid pAMY by a known method to thereby construct the plasmid pAMY-Hyg (FERM BP-5569) (see FIG. 1).

Example 4

Hygromycin B resistance, amylase activity and substance PF1022 productivity of transformant obtained by transformation by plasmid pAMY-Hyg In accordance with the procedure described in Example 1, the strain PF1022 (FERM BP-2671) was transformed by using the plasmid pAMY-Hyg. In 10 strains among the transformants thus obtained, hygromycin B resistance was confirmed according to the method described in Example 1. As a result, all of them could grow in the presence of hygromycin B at a concentration of 200 µg/ml.

Next, as a production medium, one comprising 2.0% of glucose, 5.0% of starch, 0.8% of wheat germ, 1.3% of soybean cake, 0.38% of meat extract, 0.13% of sodium chloride and 0.15% of calcium carbonate and having a pH of 7.0 before sterilization was prepared. By using this production medium, the above-mentioned transformants were cultured at 26° C. for 6 days.

The amylase activity of the culture supernatant was measured in accordance with the protocol of the Amylase Test Wako (mfd. by Wako Pure Chemical Industries, Ltd.), i.e., the iodostarch method. More particularly, a 0.25M phosphate buffer solution (pH 7.0, containing 400 µg/ml of soluble starch) and a 0.01N solution of iodine were used respectively as the substrate buffer and the color developing solution. The specimen (the culture supernatant) was added to the substrate buffer at 37° C. After a given period of time had lapsed, the color developing solution and distilled water were added to the mixture thus obtained and the resulting mixture was subjected to colorimetric determination. In the colorimetric determination, use was made of a spectrophotometer Hitachi u-2000 (mfd. by Hitachi, Ltd.). From the determined results thus obtained, the amylase activity of the culture supernatant was calculated by the Caraway method.

As a result of the determination, the parent strain (the strain PF1022) showed an amylase activity of 16 Units/ml, while the transformants showed amylase activities about 100 times higher than that of the parent strain. In particular, the strain TF10 showed an amylase activity of 34,171 Units/ml, namely, about 1,500 times higher than that of the parent strain. Further, the substance PF1022 productivities of the transformants amounted to about 120 to 150% of that of the parent strain. Thus, it was confirmed that the productivity had been elevated compared with the parent strain (see Table 1).

TABLE 1

| Strain | Hygromycin B resistance (200 μg/ml) | Amylase activity (Units) | Substance PF1022 productivity (μg/ml) |
| --- | --- | --- | --- |
| TF1 | + | 1765 | 1427 |
| TF2 | + | 906 | — |
| TF3 | + | 1445 | 1423 |
| TF4 | + | 2596 | — |
| TF5 | + | 2131 | 1414 |
| TF6 | + | 1647 | — |
| TF7 | + | 30 | 1227 |
| TF8 | + | 22 | — |
| TF9 | + | 797 | 1301 |
| TF10 | + | 34171 | 1515 |
| parent | − | 16 | 1042 |

Chromosomal DNAs were isolated from the transformants TF6, TF7 and TF10 and the parent strain PF1022 in accordance with the method of Horiuchi et al. (see H. Horiuchi et al., J. Bacteriol., 170, 272–278(1988)). These DNAs were digested with a restriction enzyme BamHI or EcoRI and the DNA fragments thus obtained were subjected to southern hybridization analysis by using pAMY-Hyg as a probe. The southern hybridization was effected in accordance with the protocol of an ECL direct nucleic acid labeling and detection system kit (mfd. by Amershem). More particularly, the southern hybridization was effected under the following conditions.

0.25N hydrochloric acid and a 0.5M aqueous solution of sodium hydroxide were employed as solutions for denaturing the DNAs. Hybond-N+ was employed as a transfer membrane. A 0.3M trisodium citrate-3M sodium chloride solution (pH 7.0) (20×SSC) was used for, e.g., washing in the capillary blotting and other steps. After the blotting, the transfer membrane was alkali-fixed by using a 0.4M aqueous solution of sodium hydroxide. Labeled pAMY-Hyg was used as a probe. The hybridization was effected at 42° C. by using a hybridization buffer containing 5% of a blocking reagent and 0.5M of sodium chloride. For washing of the probe after the hybridization, 0.5×SSC containing 6M of urea and 0.4% of sodium dodecyl sulfate (SDS) and 2×SSC free from these additives were used. For the detection, luminescence by the luminol oxidation reaction was performed and the luminescence was detected by autoradiography.

As a result, DNA fragments hybridizable with pAMY-HYg employed as the probe were detected from the DNAs of all of the transformants tested. In contrast thereto, no such DNA fragment was detected from the DNA of the parent strain. This indicated that the gene originating in the plasmid pAMY-Hyg had been transduced into the transformants and, as the result, the transformants had acquired the character of the hygromycin B resistance and a high amylase activity.

Example 5

Analyses of chromatographic fractions of culture supernatants of transformant and parent strain The culture supernatant of the strain TF10 obtained in Example 4 was filtered through a millipore filter (mfd. by Millipore, 0.45 μm). 500 μl of the filtrate was subjected to a chromatographic analysis |buffer A: 50 mM Tris-HCl (pH 7.0), buffer B: 50 mM Tris-HCl (pH 7.0), 1M NaCl|with an FPLC apparatus (mfd. by Pharmacia Biotech, column: RESOURCE Q).

Figure 2:
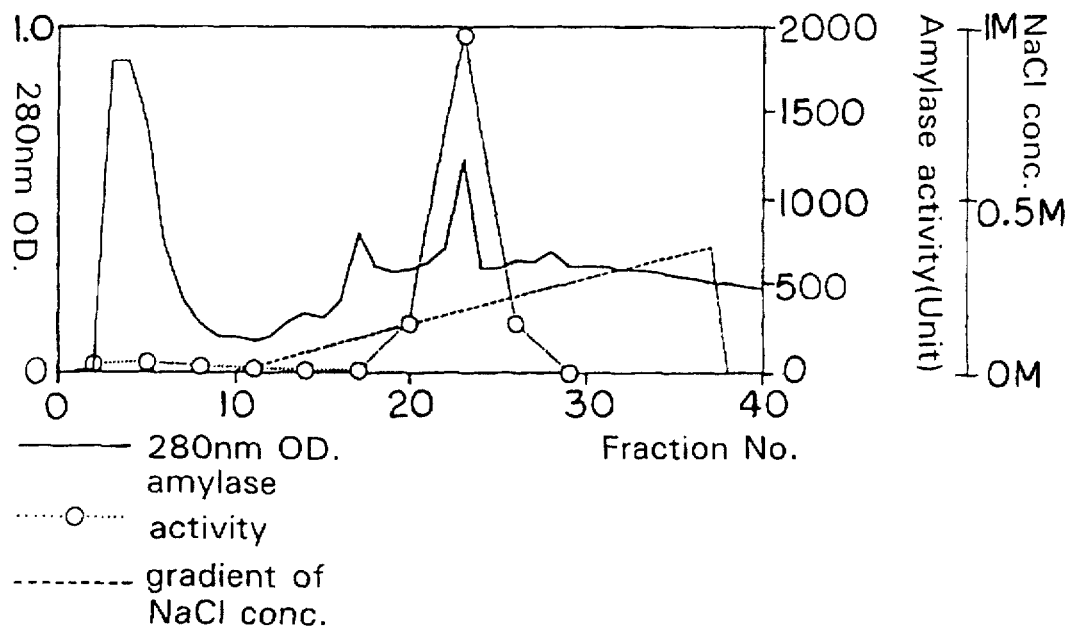
FIG. 2 is a graph showing the results of the amylase activity determination of the chromatographic fractions of the culture supernatant of the transformant.

The elution of *Taka amylase* was confirmed by not only monitoring the absorbance ($OD_{280}$) but also determining the amylase activities of specified fractions. As a result, it was confirmed that Taka amylase was eluted into the fraction with an NaCl concentration of 0.2M (see FIG. 2).

Figure 3:
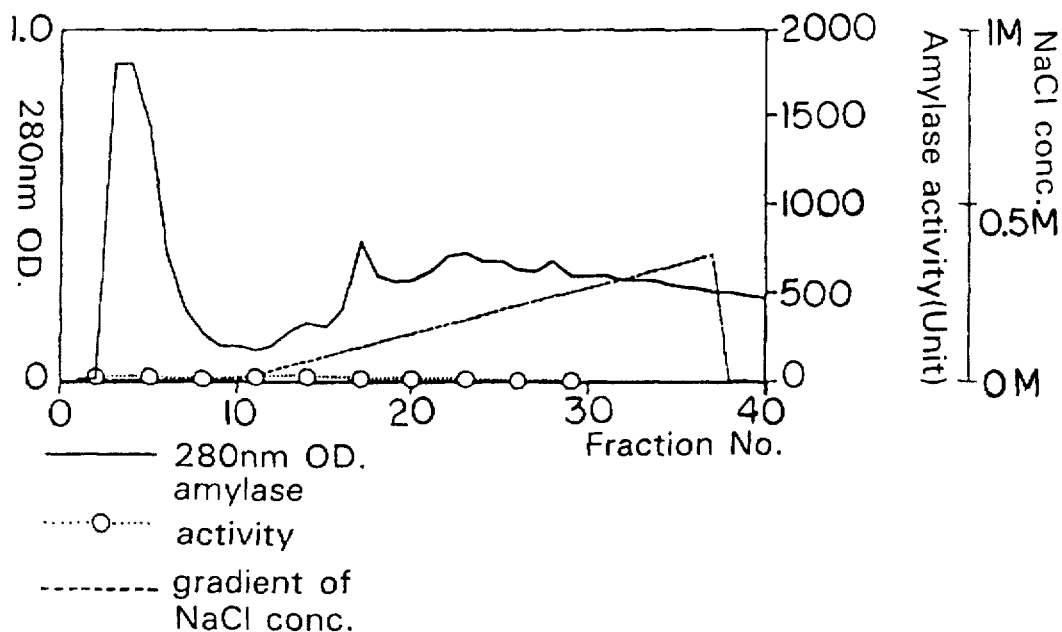
FIG. 3 is a graph showing the results of the amylase activity determination of the chromatographic fractions of the culture supernatant of the parent strain (the host).

Although the culture supernatant of the strain PF1022, which was the parent strain, was also analyzed in the same manner, the elution of *Taka amylase* was not confirmed (see FIG. 3).

Further, the amount of the protein in the culture supernatant of the strain TF10 was determined by comparison with the result of the chromatographic analysis of the standard substance of *Taka amylase*. As the result, it was found that the *Taka amylase* enzyme protein thus produced was contained in the culture supernatant of the strain TF10 at a concentration of 5 g/l (the average value of the amounts of the protein in the fractions).

We claim:

1. A transformant which produces substance PF1022 and is obtained by transforming Agonomycetales Hyphomycetes PF1022 (FERM BP-2671), and derivatives thereof which produce substance PF1022, by a plasmid constructed with a promoter, a terminator, a marker gene and a target *Aspergillus niger* alpha amylase gene.

2. The transformant as described in claim 1, wherein the marker gene is a drug-resistance gene or an auxotrophic gene.

3. The transformant as described in claim 1, wherein the promoter and the terminator are the promoter and terminator of a trpC gene from *Aspergillus nidulans* and the marker gene is a hygromycin B-resistance gene from *Escherichia coli*.

4. A process for producing substance PF1022 which comprises the step of culturing the transformant as described in claim 1 to produce product substance PF1022 and the step of recovering the product from the culture thus obtained.

5. A method of elevating the substance PF1022 productivity of Agonomycetes Hyphomycetes PF1022 (FERM BP-2671), and derivatives thereof which produce substance PF1022, which comprises the transforming of Agonomycetes Hyphomycetes PF1022 (FERM BP-2671), and derivatives thereof which produce substance PF1022, with a plasmid constructed with a promoter, a terminator, a marker gene and a target *Aspergillus niger* alpha amylase gene.

6. A method for transformation which comprises transforming Agonomycetales Hyphomycetes PF1022 (FERM BP-2671) by using a plasmid constructed with a promoter, a terminator, a marker gene and a target *Aspergillus niger* alpha amylase gene.

* * * * *